(12) United States Patent
Hamilton et al.

(10) Patent No.: US 9,943,712 B2
(45) Date of Patent: Apr. 17, 2018

(54) COMMUNICATION AND SPEECH ENHANCEMENT SYSTEM

(71) Applicant: Delores Speech Products, LLC, Wellesley, MA (US)

(72) Inventors: John Hamilton, Wilmington, DE (US); Christopher McDivit, Irvine, CA (US); Charles G Sproule, IV, Malvern, PA (US)

(73) Assignee: DOLORES SPEECH PRODUCTS LLC, Wellesley, MA (US)

(*) Notice: Subject to any disclaimer, the term of this patent is extended or adjusted under 35 U.S.C. 154(b) by 113 days.

(21) Appl. No.: 14/853,612

(22) Filed: Sep. 14, 2015

(65) Prior Publication Data

US 2016/0001110 A1    Jan. 7, 2016

Related U.S. Application Data

(63) Continuation-in-part of application No. 14/034,020, filed on Sep. 23, 2013, now Pat. No. 9,344,781.
(Continued)

(51) Int. Cl.
    *H04R 1/00*     (2006.01)
    *A62B 18/08*    (2006.01)
(Continued)

(52) U.S. Cl.
    CPC .......... *A62B 18/08* (2013.01); *A61B 5/0205* (2013.01); *A61B 5/14552* (2013.01);
(Continued)

(58) Field of Classification Search
    CPC ........ H04R 1/02; H04R 1/028; H04R 1/1083; H04R 1/14; H04R 2201/107; G10L 21/02;
(Continued)

(56) References Cited

U.S. PATENT DOCUMENTS

| 2,165,124 A | 7/1939 | Ballantine |
|---|---|---|
| 2,950,360 A | 8/1960 | Duncan |

(Continued)

FOREIGN PATENT DOCUMENTS

| CN | 102143437 | 8/2011 |
|---|---|---|
| CN | 104937580 | 9/2015 |

(Continued)

OTHER PUBLICATIONS 201380061038.3, "Office Action," dated Jan. 4, 2017, 16 pages.
(Continued)

*Primary Examiner* — Sean H Nguyen
(74) *Attorney, Agent, or Firm* — Kilpatrick Townsend & Stockton LLP

(57) ABSTRACT

A communication and speech enhancement system featuring a first transducer designed to be temporarily affixed to a human such as a hospital patient to convert the audible vibrations of human speech into an electrical signal. The transducer provides this electrical signal to one or more electronic modules which modify and enhance the signal. The enhanced signal may then be amplified and converted back into audible sound by means of a second transducer. A user of the system controls the electronic modules through a user interface. In an embodiment, one or both of the user interface and second transducer feature smooth surfaces amenable to cleaning sterilizing with liquid agents.

20 Claims, 4 Drawing Sheets

Related U.S. Application Data

(60) Provisional application No. 61/849,326, filed on Jan. 23, 2013, provisional application No. 61/744,385, filed on Sep. 24, 2012.

(51) Int. Cl.

| | | |
|---|---|---|
| *H04R 1/14* | (2006.01) | |
| *A61M 16/00* | (2006.01) | |
| *A61B 7/00* | (2006.01) | |
| *A61B 5/00* | (2006.01) | |
| *A61B 5/1455* | (2006.01) | |
| *A61B 5/0205* | (2006.01) | |
| *A61M 16/04* | (2006.01) | |
| *H04R 1/10* | (2006.01) | |
| *H04R 5/033* | (2006.01) | |
| *A61M 16/06* | (2006.01) | |
| *H04R 1/02* | (2006.01) | |
| *G10L 21/0364* | (2013.01) | |
| *H04R 23/00* | (2006.01) | |
| *G10L 21/0208* | (2013.01) | |
| *G10L 21/057* | (2013.01) | |

(52) U.S. Cl.
CPC .......... *A61B 5/7282* (2013.01); *A61B 7/003* (2013.01); *A61M 16/0051* (2013.01); *A61M 16/0069* (2014.02); *A61M 16/044* (2013.01); *A61M 16/06* (2013.01); *G10L 21/0364* (2013.01); *H04R 1/028* (2013.01); *H04R 1/1016* (2013.01); *H04R 1/1066* (2013.01); *H04R 1/14* (2013.01); *H04R 5/0335* (2013.01); *A61M 16/0468* (2013.01); *A61M 2205/3375* (2013.01); *A61M 2205/3553* (2013.01); *A61M 2205/3592* (2013.01); *A61M 2205/505* (2013.01); *G10L 21/0208* (2013.01); *G10L 2021/0575* (2013.01); *H04R 1/1083* (2013.01); *H04R 23/008* (2013.01); *H04R 2201/107* (2013.01); *H04R 2420/07* (2013.01)

(58) Field of Classification Search
CPC .............. G10L 13/00; A61M 16/0468; A61M 2205/3375; A61M 2205/3592; A61M 2205/505
USPC ........................................................ 381/385
See application file for complete search history.

(56) References Cited

U.S. PATENT DOCUMENTS

| | | |
|---|---|---|
| 3,180,333 A | 4/1965 | Lewis |
| 3,265,153 A | 8/1966 | Burroughs |
| 3,588,359 A | 6/1971 | Cribb |
| 3,746,789 A | 7/1973 | Alcivar et al. |
| 4,072,831 A | 2/1978 | Joscelyn |
| 4,143,648 A | 3/1979 | Cohen et al. |
| 4,311,872 A | 1/1982 | Davis |
| 4,537,276 A | 8/1985 | Confer |
| 4,607,383 A | 8/1986 | Ingalls |
| 4,736,740 A | 4/1988 | Parker et al. |
| 4,799,263 A | 1/1989 | Bänziger et al. |
| 5,163,093 A | 11/1992 | Frielingsdorf et al. |
| 5,224,473 A | 7/1993 | Bloomfield |
| 5,259,373 A | 11/1993 | Gruenke et al. |
| 5,307,793 A | 5/1994 | Sinclair et al. |
| 5,463,693 A | 10/1995 | Birli et al. |
| 5,503,141 A | 4/1996 | Kettl et al. |
| 5,572,990 A | 11/1996 | Berlin |
| 5,626,132 A | 5/1997 | Miller |
| 5,802,198 A | 8/1998 | Beavers et al. |
| 5,895,537 A | 4/1999 | Campbell |
| 6,164,277 A | 12/2000 | Merideth |
| 6,174,278 B1 | 1/2001 | Jaeger et al. |
| D441,353 S | 5/2001 | Sun |
| 6,382,206 B1 | 5/2002 | Palazzotto et al. |
| 6,606,388 B1 | 8/2003 | Townsend et al. |
| 6,950,682 B2 | 9/2005 | Takeda et al. |
| 6,997,178 B1 | 2/2006 | Reynaud |
| 7,386,137 B2 | 6/2008 | Combest |
| 7,394,905 B2 | 7/2008 | Miller et al. |
| 7,457,427 B2 | 11/2008 | Birli et al. |
| 7,493,899 B2 | 2/2009 | Davies |
| 7,639,824 B2 | 12/2009 | Franzen |
| 2001/0012373 A1 | 8/2001 | Graumann |
| 2002/0110252 A1 | 8/2002 | Liu |
| 2003/0016211 A1 | 1/2003 | Woolley et al. |
| 2005/0069160 A1 | 3/2005 | Kehoe |
| 2005/0244020 A1* | 11/2005 | Nakajima ............... G10L 15/24 381/151 |
| 2005/0256594 A1 | 11/2005 | Wong et al. |
| 2006/0126886 A1 | 6/2006 | Combest et al. |
| 2007/0165885 A1 | 7/2007 | Chou |
| 2009/0007596 A1 | 1/2009 | Goldstein et al. |
| 2009/0111527 A1 | 4/2009 | Richardson et al. |
| 2009/0161893 A1 | 6/2009 | Hironaka et al. |
| 2009/0175478 A1* | 7/2009 | Nakajima ................ H04R 1/46 381/361 |
| 2009/0205662 A1 | 8/2009 | Kwok et al. |
| 2010/0262425 A1* | 10/2010 | Tanabe .................... G06T 5/002 704/233 |
| 2010/0324374 A1 | 12/2010 | Kim et al. |
| 2011/0051944 A1 | 3/2011 | Kirkpatrick |
| 2011/0125060 A1 | 5/2011 | Telfort et al. |
| 2012/0206384 A1 | 8/2012 | Marsden et al. |
| 2013/0317753 A1* | 11/2013 | Kamen ............... G06F 19/3412 702/19 |
| 2015/0202395 A1* | 7/2015 | Fromentin ............ A61M 16/00 128/207.16 |

FOREIGN PATENT DOCUMENTS

| | | |
|---|---|---|
| DE | 734732 | 4/1943 |
| EP | 2898419 | 7/2015 |
| IN | 2288CHENP2015 | 7/2016 |
| JP | 2002271881 | 9/2002 |
| JP | 2008505538 | 2/2008 |
| JP | 2008543383 | 12/2008 |
| WO | 2017048485 | 3/2017 |

OTHER PUBLICATIONS

Avdoshin , "An Optoelectronic Voice Communications System," Telecommunications and Radio Engineering, Scripta Technica,Inc vol. 43, No. 1, Jan. 1, 1988, pp. 92-94.
PCT/US2016/049107, "International Search Report and Written Opinion," dated Jan. 25, 2017, 20 pages.
Widrow et al., "Adaptive Noise Cancelling: Principles and Applications," Proceedings of the IEEE, vol. 63, No. 12, Dec. 1, 1975, pp. 1692-1716.
U.S. Appl. No. 14/034,020, "Notice of Allowance", dated Mar. 1, 2016, 10 pages.
U.S. Appl. No. 14/034,020, "Final Office Action", dated Mar. 18, 2015, 23 pages.
U.S. Appl. No. 14/034,020, "Final Office Action", dated Sep. 23, 2015, 28 pages.
U.S. Appl. No. 14/034,020, "Non-Final Office Action", dated Jul. 31, 2014, 18 pages.
CN201380061038.3, "Office Action", dated Jun. 8, 2015.
EP13839511.6, "Extended European Search Report", dated May 27, 2016, 10 pages.
PCT/US2013/000216, "International Search Report and Written Opinion", dated Nov. 14, 2013, 3 pages.
EP13839511.6, "Office Action," dated May 29, 2017, 5 pages.

\* cited by examiner

COMMUNICATION AND SPEECH ENHANCEMENT SYSTEM

CROSS-REFERENCES TO RELATED APPLICATIONS

This application is a continuation-in-part of U.S. patent application Ser. No. 14/034,020 entitled "Communication and Speech Enhancement System," filed on Sep. 23, 2013, which claims the benefit of U.S. Provisional Patent Application No. 61/744,385, filed on Sep. 24, 2012, as well as U.S. Provisional Patent Application No. 61/849,326, filed on Jan. 23, 2013, both in the names of John Hamilton et al. The entire disclosures of each of these commonly owned patent applications are expressly incorporated herein by reference.

BACKGROUND

Field of the Invention

The instant invention relates to the field of clinical communication with patients. More specifically the invention features a system which allows verbal communication by persons wearing respiratory assistance apparatus, the system featuring a user interface and/or an audio output transducer that is easily cleaned and sanitized Discussion of Related Art Just in the medical field alone, there are a number of different positive pressure ventilators. Among the most common are CPAP, Bi-PAP and A-PAP. C-PAP stands for "Continuous Positive Airway Pressure". This ventilator provides the patient with a constant positive air pressure to keep the patient's airways open and prevent obstruction due to muscle relaxation. Bi-PAP, or "Bilevel Positive Airway Pressure", deliver two pressure levels instead of one, and which pressure levels are synchronized to assist in the inhalation and exhalation processes. A-PAP is a species of C-PAP apparatus that automatically titrates a patient's pressure.

There are a number of situations in which a person needs to wear a respirator, either of the mask or the full-face variety, in order to be able to breathe adequately and properly. An almost universal problem with such respirators is that it makes normal verbal communication difficult, as the mask portion of the respirator tends to muffle the sound. In addition, a number of such respirators are "active" in the sense that they assist in inhalation and exhalation of air or oxygen, e.g., by means of a pump. The pumped air can make a "whooshing" sound that competes with the patient's speech, thus adding to the difficulty for the listener.

One potential solution to this problem is to introduce electronics, with electrically-powered transducers such as microphones and speakers. There are existing systems for communications with persons wearing respirators and face masks. Two examples include fire-fighting and scuba communication devices which allow persons wearing such equipment to communicate verbally with remote persons. These systems typically involve communication with remote persons through a wireless link or umbilical cable to remote devices. Thus, these systems are not arranged for general listening, but instead require a receiver for each person who wishes to hear the communication. Further, such a system requires a cable connection or some form of radio transmission.

Another related system is the one that physicist Stephen Hawking uses to verbalize with others. But this system is not processing his actual speech, but instead is synthesizing speech based on a non-speech input from him. As such, the "speech" sounds unnatural, and fails to convey the tonal qualities and emotions of the speaker.

Another issue that arises in the health care setting, however, is sterilization. Clinical and medical applications require equipment to be cleaned between uses. Traditional control inputs on medical devices employ knobs, buttons, and switches that inherently possess small openings, overhangs, ridges, and other surfaces that may capture contaminants, and are not easily cleansed. Typical practice requires devices to be either enclosed with a sterile, disposable covering during use, or to be disassembled and hand cleaned by technical specialists. The drawbacks of a sterile cover are that it must possess some type of opening to accommodate electrical leads while maintaining a sterile condition. In addition, the cover material naturally inhibits accurate view of indicators and displays, and the texture and slick nature of transparent cover materials reduces accurate manipulation of control knobs and switches. Manual cleaning and disassembly by skilled technicians adds substantially to the operational cost of equipment, and exposes service personnel to potentially infectious disease.

Traditional audio output devices consist of an electromechanical transducer (speaker), inside of an enclosure which possesses an opening through which the sound may propagate. These openings may be covered with a perforated rigid material, a screen, a permeable cloth/textile, or membrane/laminate sheet of sufficiently thin cross section to allow resonation in harmony with the transducer thereby allowing sound to exit the enclosure.

In cases of perforated, screen, or textile coverings, contaminants are permitted to enter the perforations or fabric, thereby creating an unsanitary condition that is not easily cleaned. In cases of the thin membrane covering; while the membrane surface maintains advantageous non-porous properties, the arrangement suffers audio output attenuation, signal degradation, and distortion due to the air gap between the speaker diaphragm and the membrane, as well as from the mechanical properties of the membrane itself which acts as a semi-rigid passive radiator.

This new device addresses both the issues related to control inputs and audio output.

BRIEF SUMMARY

The present invention features a communication system for persons wearing respiratory apparatus. The system provides the means for normal verbal communication that is otherwise impossible when wearing respiratory apparatus. In the medical treatment setting, communication can occur in the same room with the patient and provides patients the ability to communicate verbally with doctors, staff, and visitors.

In accordance with the present invention, a transducer is affixed to the patient to convert audible vibrations to an electrical signal having audio range frequencies. The transducer provides this electrical signal to electronic modules which modify and enhance the signal. The enhanced signal is then amplified and converted back into an audible sound of speech by means of another transducer.

The various electronic modules are controlled by a user of the system or device by means of a user interface. To accommodate user input, the device possesses at least one external surface of the user interface having a dielectric constant favorable to transmission of a small electric field suitable for use with capacitive touch sensor circuits on the reverse side. These circuits allow the user to provide an input simply by placing a finger over the sensor area. The external surface is constructed of a sheet of material such as glass, acrylic, carbon fiber, fiberglass, plastic, combination laminate, or other suitably strong, smooth material. This surface, being smooth and free of buttons, switches, openings, overhangs, ridges, or crevices, allows for easy disinfecting with standard cleaning solutions and by non-specialist personnel.

The audio output portion of the system or device is also designed with ease of cleaning and sterilizing in mind. In particular, and rather than use a loudspeaker as the diaphragm for the second transducer, audio output is provided by a solid surface exciter such as by means of those known in the art, for example, as disclosed in U.S. Pat. No. 7,386,137.

In one embodiment, the solid surface exciter is affixed to the inside surface of the surface material thereby employing the surface material as the transducer diaphragm. By placing the user input devices on the same surface area as the audio output device, overall device size may be reduced.

Additional user feedback may be provided though haptics which employs a haptic motor producing tactile feedback through the surface material to acknowledge and confirm a user input.

Thus, in one of its embodiments, this new device addresses both the issues related to control inputs and audio output through a novel application combining capacitive input detection and a solid surface transducer.

Additional features such as wireless signaling and noise cancellation will also be described.

In some embodiments, a system for providing verbal communication ability to persons wearing a respiratory apparatus, which would otherwise prevent or restrain verbal communication, that has at least one transducer attached to the body of the person near the throat, proximate to the vocal folds, for converting sounds into a signal. The system can also have processing capability, which may be hardware or software, and memory capability which may be a buffer for storing the signal and processed signals developed therefrom. The system can receive the signal from the transducer, process and/or filter the signal to isolate frequencies associated with vocalizations and/or filter the signal based on patterns of the signal (such as removing sounds not caused by vocalization from the audio signal based on, for example, repetitive patterns or from one or more other signals), and output the processed and/or filtered signal.

Systems such as those described above may use high-gain optical transducers, or any other suitable high-sensitivity transducer or microphone, or an array of multiple transducers or microphones. In some cases, multiple transducers can be used to obtain multiple audio signals which can be selectively recombined. In some cases, the combination may be used to correct for a low signal at one or more positions of a subset of the multiple transducers, i.e., if a practitioner places an array of microphones at multiple locations around the neck of a patient, then one or more of the microphones is likely to be positioned at an optimal receiving position.

In some embodiments, additional microphones beyond the first (or beyond the first plurality of microphones) can be placed on or within portions of the respiratory apparatus, such as on or in a face mask, on or near an endotracheal tube, or on or near a ventilator. The additional microphones can be used to obtain an audio signal from one or more of said components of the respiratory apparatus. The system can, using an audio signal or signals from the components, mitigate the interference of said audio signal(s) by cancelling a portion of the first audio signal that carries the vocalizations, in order to enhance the clarity of the vocalizations.

In some cases, the audio signal(s) from a transducer or transducers attached with the patient and/or the transducer or transducers attached with the respiratory apparatus can be used to obtain information concerning the patient and/or respiratory apparatus. For example, an audio signal from a transducer attached with the patient can be used to determine attributes of patient health such as: heartrate, swallowing, agitation, movement, or other suitable attributes. An audio transducer attached with the respiratory apparatus can likewise detect sounds associated with: an air leak, a low pressure, any abnormal function that impacts pressure or flow rate, or other suitable attribute. The detection of any of the above attributes may cause the system to provide an alert or a warning for physicians or caretakers.

In some cases, the system can also cause a change in the function of the respiratory apparatus. For example, in a noninvasive respiratory apparatus, the system can detect sounds associated with a patient attempting to speak (such as an intake of breath, a swallow, a pause in breathing, or other suitable signal) and temporarily reduce or suspend the pressure of the positive airflow supplied, so as to reduce the volume of the sound of rushing air associated with the respiratory apparatus and/or to reduce the pressure against which the patient has to fight to speak. In an invasive respiratory apparatus, where the patient is intubated, the system can detect sounds in the same or similar manner and cause an inflatable endotracheal cuff to partially deflate, allowing air to escape the lungs with which the patient can vocalize and/or to temporarily reduce or suspend the pressure of the airflow supplied, for the same or similar reasons as described above. In addition to signals from the present device being employed to modulate operation of the respirator, signals from the respirator, or from a pressure transducer in the mask, can modulate operation of the device to mute the output during an inhalation cycle, allowing a greater signal to noise ratio, in accordance with embodiments.

DETAILED DESCRIPTION

Figure 1:
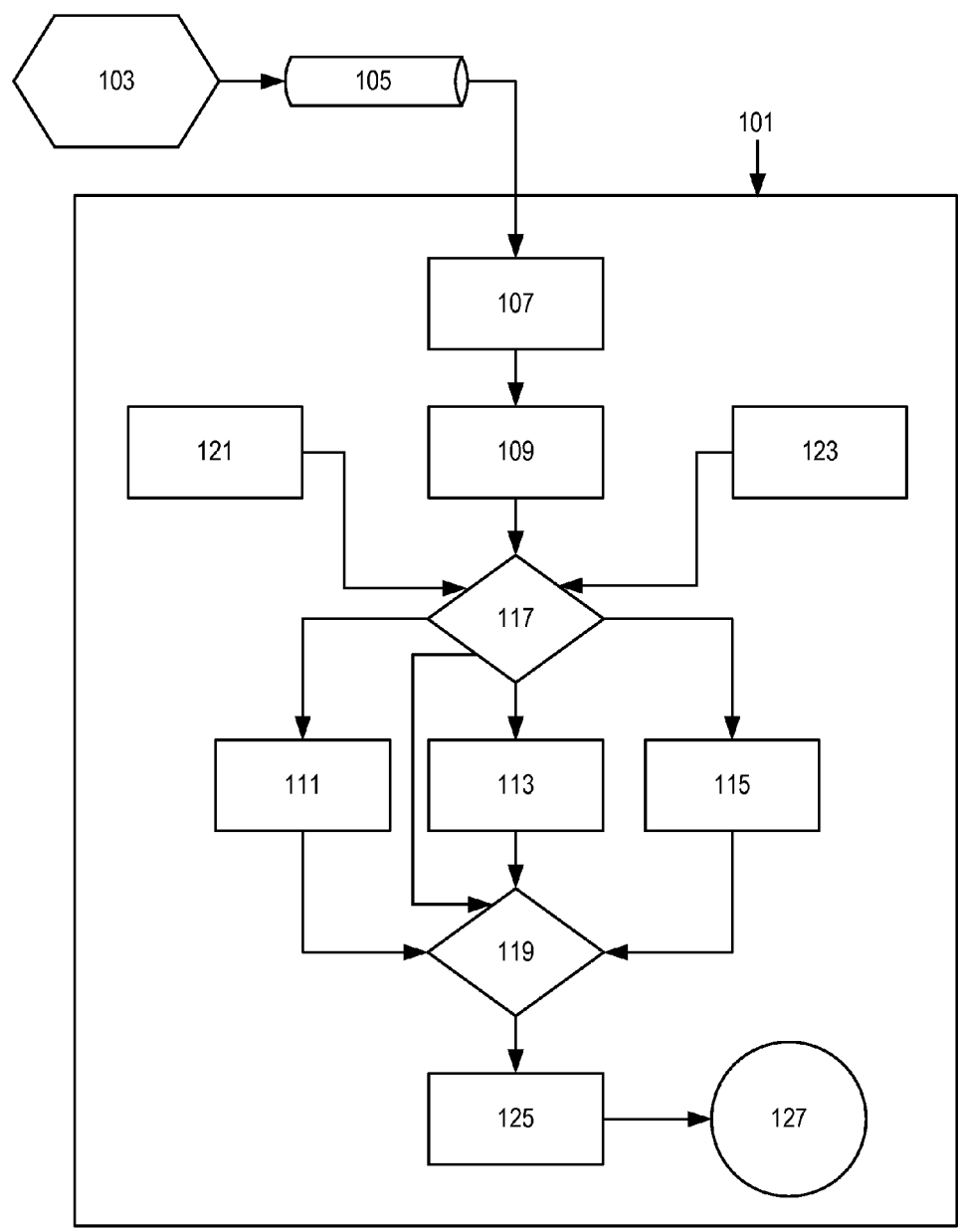
FIG. 1 is a schematic block diagram showing the conversion of sound such as speech into and out of an audio signal, and the path of that signal as it is processed.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The instant invention pertains to communication systems for persons wearing respiratory apparatus that otherwise would prevent verbal communication. One aspect of the invention pertains to medical patients who wear such respirators to help them breathe. In this aspect of the invention, one embodiment of the invention can be a stand-alone system that can be used with existing respirator equipment such as C-PAP, A-PAP and Bi-PAP. Another embodiment of the system has the communications system integrated or built into the respirator equipment ("machine").

The communication and speech enhancement system of the instant invention features a first transducer such as a microphone whose electrical signal output is connected by wire or wirelessly to a signal processor to enhance intelligibility. Such connection may be referred to as an "interface". Operating power for the system is electrical in nature and may be supplied by local line voltage or batteries, or line voltage with battery backup.

The system specifically modifies the signal to produce intelligible speech at sufficient listening levels for clinical applications. The output of the signal processing is a "line level" electrical signal at audio frequencies. This electrical signal may then serve as the audio input for an amplifier for a second transducer, the audio output transducer.

The first transducer is arranged to be removably attached to the human wearer on the throat at or near the larynx ("voice box"). In one embodiment, the means for attachment is a strap which may be elastic and which may feature fasteners known in the art such as VELCRO hook-and-loop attachment system. In an alternate embodiment, sometimes referred to as "the self-stick attachment method", the first transducer may be integrated with a sterile fabric swatch or bandage incorporating a self-adhesive and applied directly to the patient in a manner similar to an EKG sensor. In a second alternate embodiment, the first transducer may be mounted in the respiratory mask component of the respiratory machine. This first transducer may be hermetically sealed to allow cleaning and disinfecting with liquid disinfectants. In each of these embodiments, the first transducer, e.g., microphone, may be cylindrically shaped, and may be mounted in a ring-shaped housing, which is then attached to the strap, fabric swatch/bandage or respirator. The housing may feature one or more protrusions that extend from the circumference into the interior space defined by the ring, the protrusions serving to prevent the cylindrically shaped first transducer from extending too far into the housing. In this way, the first transducer can be maintained at a desired distance from the larynx.

From the interface, the electrical signal travels to the speech processing unit, which here is termed the "Speech Enclosure". The overall system of the instant invention may optionally include a main amplifier and the second transducer, and these two devices may also be housed in the speech enclosure.

At a minimum, the audio processing unit features a high pass filter to remove bass frequencies below a certain threshold frequency. Functionally, this action eliminates or at least greatly reduces the very low frequencies associated with impacts and physical contact with the first transducer.

The audio processing unit optionally may feature other components for additional specific processing of the speech. These other components include volume and tone controls, a dynamics processor, an equalization circuit, a feedback suppressor, and processing sequence controls.

The volume and tone controls are similar in function to those found on common audio equipment such as a radio, television or portable audio equipment such as a portable, tape, CD, or MP3 player, or "boombox".

The dynamics processor controls the dynamic range of the speech, that is, the range from quiet to loud, that is, the intensity range. Here, this typically means compressing, or "limiting the headroom" of the very loud sounds. Optionally, the dynamics processor may also expand or amplify the very soft or quiet sounds.

The equalization circuit is similar to that found on better quality stereo systems. Here, instead of having a pair of controls for "bass" and "treble", the audio spectrum is broken into a plurality such as half a dozen or more segments or "channels", each of which can be controlled in terms of volume (enhanced or suppressed) independently of the other channels.

The feedback suppressor is designed to do exactly that-suppress audio feedback. Feedback typically manifests itself as a high pitched squeal or howl, and results from the output of a loudspeaker re-entering the microphone from which the output originated in excess quantities. Feedback is most likely to occur when the microphone is too close or aimed too much toward the loudspeaker. The feedback suppressor works by providing a time-based delay, a notch-type filter, or both.

The processing sequence controls provides the user of the system with control over which of the optional components of the speech processing unit are activated, and in which order. The order in which the audio signal is processed affects the signal. Thus, the user is able to experiment with different signal paths to obtain the best results, for example, in terms of speech intelligibility.

The invention will now be further described with reference to FIG. 1, which illustrates one embodiment of the invention. Referring to FIG. 1, the audio processing unit, main amplifier and audio output transducer are housed in a single "speech enclosure", as indicated by the large box 101. Outside of this box to indicate its physical separateness is the first transducer 103 such as an audio microphone. The first transducer produces an electrical signal that is connected with wires or wirelessly to the speech enclosure 101 through the interface unit 105.

Once inside the speech enclosure 101, the signal is first amplified, for example, to "line level" by means of a high gain pre-amp 107. Next, the signal passes through the high pass filter 109. From there, the signal may pass through one or more other processors such as the dynamics processor 111, the equalization circuit 113 and/or the feedback suppressor 115. The signal path processor 117 and signal return path processor 119, as activated by the processing sequence controls 121, a user interface device, determines which of these other signal processors the signal passes through, and in what order. This speech enclosure also features the volume/tone control 123. After completing signal processing, the signal passes through the main audio amplifier 125 and into the second transducer, which may be a loudspeaker 127. Here, the audio signal is converted into pressure pulses of air that are heard as sound by the ear and brain of the human body.

In a third alternate embodiment of the invention, a given processing element may be duplicated, as long as the duplicate is not placed immediately adjacent the original processing element. For example, it may be desirable for the audio processing unit to contain two equalizer circuits, with the dynamics processor element placed between them.

In a fourth alternate embodiment of the invention, the audio signal processing could employ negative feedback in a desirable manner. Specifically, one could invest a portion of the output signal from the audio processing unit, i.e., make its polarity negative, filter out selected frequencies or dynamics from the signal, and the insert it back into the input stage of the audio processing unit. Because of the inverted polarity, the balance of the original and inverted signals cancel each other out, leaving the selected frequencies or dynamics from the original signal to pass through.

Wireless Aspect

In a second major aspect of the invention, instead of being routed to the interface/speech enclosure, the output of the first transducer may be sent wirelessly instead to a receiving device such as a Personal Digital Assistant (PDA) or cell phone. Specifically, the microphone housing may incorporate a battery powered radio transmitter. This transmitter is electrically connected to the first transducer (patient microphone) and employed to wireless conduct the electrical signal from the first transducer to the PDA, cell phone, or other device with a compatible radio receiver, (receiving device). The received signal may receive processing similar to that provided by the "Signal Processor" in the "Speech Enclosure" through a software application running on the receiving device. This embodiment allows the receiving device to output an amplified and processed signal from its onboard output speaker as well as to facilitate the ability for the wearer to conduct telephone calls, and for the signal to be integrated with other application software such as a voice recorder, speech recognition software, or environmental control systems. A variation on this embodiment includes an ear-piece speaker that is connected either by wire or wirelessly to either the first transducer/radio assembly or PDA. This ear-piece speaker attaches to the patient's ear and emits an audio signal which is received electrically from the PDA or cell phone, for example the voice of the second party in a phone call, or the audio from a software application, movie, or game.

In a fifth alternate embodiment of the invention that is at least somewhat related to the fourth alternate embodiment, and which can be used with either the first or second major aspect of the invention, the audio signal processing could employ noise cancellation technology in a desirable manner. Specifically, additional input transducers, microphones, may be employed to increase the signal-to-noise ratio and to reduce acoustic feedback. These additional input transducers capture ambient sounds in the local area of the patient. These transducers may be integrated into the "Speech Box" enclosure, integrated with the first transducer (patient microphone) assembly, or placed separately in the local environment. The electrical output signals from the additional transducers are connected by wire or wirelessly to the "Signal Processor". These signals may receive individual processing similar to that afforded the signal from transducer and be applied in whole or in part, inverted or non-inverted to the electrical signal from the first transducer to improve the signal-to-noise ratio by removing any ambient sound or acoustic feedback.

One issue with so-called throat transducers is that the mid-high and high frequencies of speech are often lacking. Accordingly, in another embodiment of the instant invention, the signal processing unit may also feature a "sibilance enhancer/synthesizer" and/or an aural exciter to add high frequency "hiss" and the mid-high frequencies of the speech, respectively, to the audio signal.

The interface provides the means by which the user of the present device may adjust the audio output such that the speech from the patient is intelligible. Another embodiment of the present invention provides at least one external surface for the interface (or "user interface") that is easily cleaned and sanitized. More specifically, this external surface of the speech enclosure may be constructed of a sheet of material such as glass, acrylic, carbon fiber, fiberglass, plastic, combination laminate, or other suitably strong, smooth material. This surface, being smooth and free of buttons, switches, openings, overhangs, ridges, or crevices, allows for easy disinfecting with standard cleaning solutions and by non-specialist personnel.

To accommodate user input, the surface material possesses a dielectric constant favorable to transmission of a small electric field suitable for use with capacitive touch sensor circuits on the reverse side. These circuits allow the user to provide an input simply by placing a finger over the sensor area. The surface material maintains a thickness and resiliency commensurate with use in the applicable commercial service. This material may be imprinted with graphics and icons indicating location and function of capacitive input controls. When clear surface material is employed the graphics may be imprinted on the reverse side, and interior illumination may be provided to highlight input control areas, or to display information and status to users. Display devices include LEDs, incandescent lamps, LCD, LED, TFT, oLED displays, and other user interface graphic devices. Illumination may change state (on/off), intensity, or color, to indicate receipt of a user input by providing a visual feedback. The capacitive sensor circuitry is affixed to the inside of the surface material and is connected to the control circuitry of the device through an electrical connection.

In addition, and in another embodiment of the present invention, the device provides an audio output transducer (the "second transducer") that also may be readily and easily cleaned and sanitized. Specifically, such audio output is provided by means of a solid surface exciter such as those known in the art, for example, as disclosed in U.S. Pat. No. 7,386,137, the entire disclosure of which is herein incorporated by reference.

The solid surface of the solid surface exciter may be a different surface than that for the user interface, but in one embodiment, it is the same surface, that is, the user interface doubles in function as the audio output surface.

In this embodiment, the second transducer is affixed to the inside surface of the surface material thereby employing the surface material as the transducer diaphragm. The lack of an air gap between the exciter motor and the surface material eliminates compression distortion, attenuation, and other signal degradation suffered by speakers mounted behind membranes. Other advantages of the solid surface material exciter relate to efficiency and output amplitude. The device allows the entire surface material to act as an acoustic radiating surface, thereby providing a much greater surface area for acoustic wave generation than a traditional speaker which employs a much smaller surface area. The transducer is driven by any standard audio amplifier, and electrically appears as a traditional speaker in circuit design. The transducer is connected to the amplifier circuit with a flexible electrical lead that allows free motion of the transducer throughout the operational frequency range and amplitude desired.

The surface material is attached to the device enclosure in a method allowing a certain range of linear motion congruent with the direction of motion generated by the solid surface exciter. The attachment method of the surface material to the enclosure is optimized to allow the surface material to resonate at a frequency desirable for the application. The surface material is isolated from the enclosure by an appropriate durometer gasket which acts as an acoustic suspension and provides for the oscillating linear motion of the surface material while maintaining seal integrity against liquid and contaminant ingress. For example, for human speech output, a resonant frequency of approximately 2000 Hz may be desirable, whereas in a dog bark prevention device a much higher resonant frequency is needed. Resonant frequency is tuned through variation of the gasket shape and contact surface area as well as the selection of material. Low and high pass filters in the exciter driver circuitry can be employed to restrict exciter frequencies to the operational design parameters of the surface material and application requirements.

By placing the user input devices on the same surface area as the audio output device, overall device size may be reduced. Since both functionalities exist in the same area, size and cost savings may be achieved without a compromise in performance.

In another aspect of the present invention, additional user feedback may be provided though haptics which employs a haptic motor producing tactile feedback through the surface material to acknowledge and confirm a user input. The haptic motor is affixed to the inside surface of the surface material and connected to control and driver circuitry through an electrical lead. The frequency of the haptic signal is selected to be outside the operating frequency of the solid surface exciter to allow user discrimination between audio output and haptic feedback.

The capacitive touch sensors, illumination and display devices, and the haptic motor may be employed on a single surface, or on multiple surfaces.

Interference Mitigation Aspect

In various embodiments, one or multiple transducers can be positioned on a patient and/or attached with portions of a ventilator device in order to actively reduce interference from non-vocal sounds. Hardware for capturing sound waves from a patient may include one or more high-gain optical microphones, or any suitable high-sensitivity audio or surface transducer for detecting sound waves or vibrations. In some cases, hardware for capturing sound waves from a patient can include one or more high-gain fiber-optic microphones. In some additional cases, multiple microphones of any suitable type can be arranged in an array, such as along a band, attached to the neck of a patient. In some cases, the microphone(s) and/or connecting cables may be nonmetallic and/or fiber-optic such that said microphone(s) can be used continuously while a patient is in an MRI machine.

Figure 2:
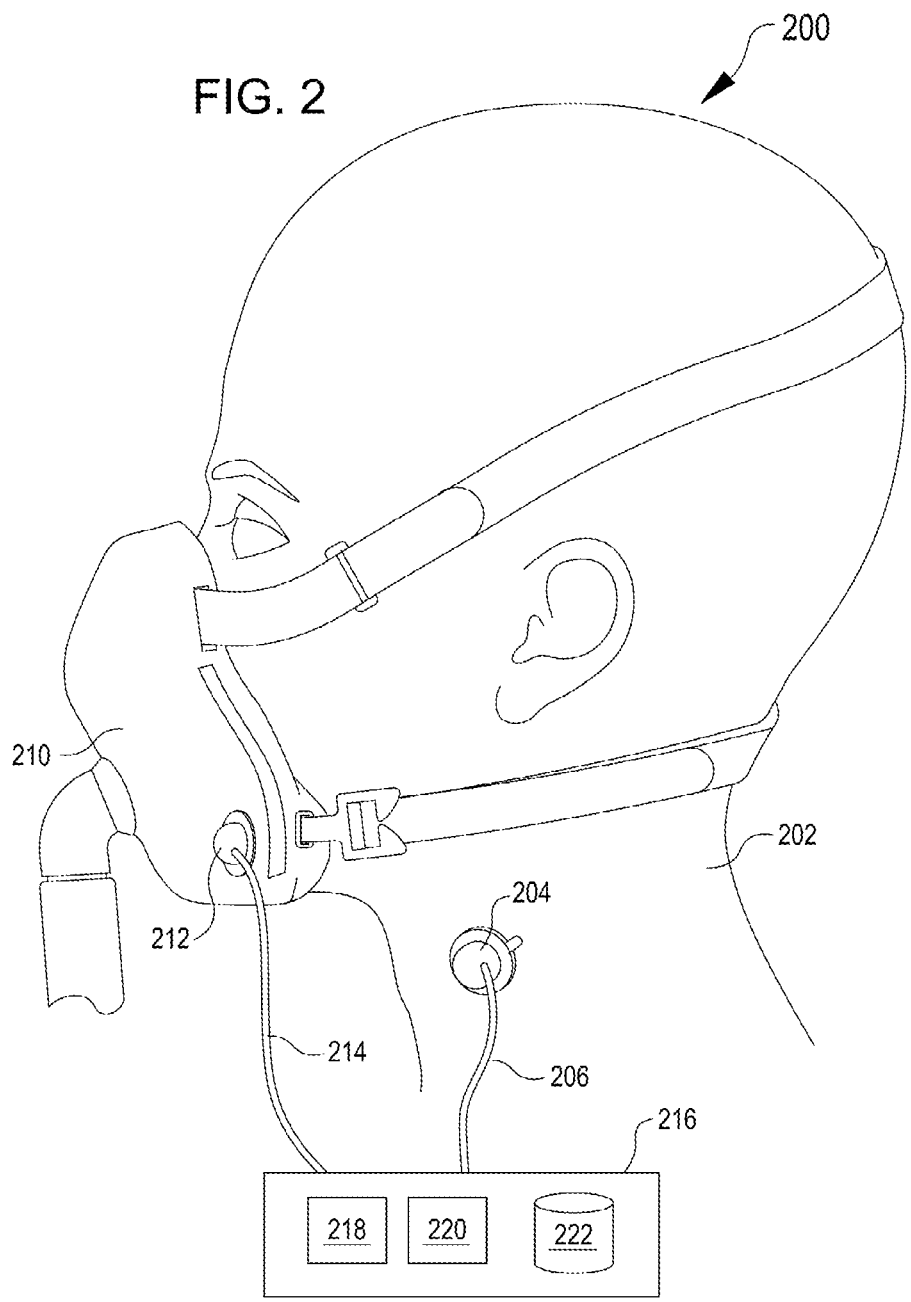
FIG. 2 is a perspective view of an exemplary speech enhancement system for use with a non-invasive ventilator, in accordance with embodiments.

FIG. 2 shows an exemplary speech enhancement system 200 for use with a non-invasive ventilator, in accordance with embodiments, that can provide mitigation of non-vocal sounds. In one aspect, multiple microphones 204, 212 can be positioned at multiple locations on a patient 202 and/or on or within equipment associated with the ventilator (not shown). For example, a dual-input sensor can include a first sensor 204 connected with the patient 202 and a second sensor 212 in a mask 210 of a non-invasive ventilator device such as a CPAP machine. The first and second sensors 204, 212 are connected (e.g., via leads 206, 214) with a processing system 216 having at least a processing module 218, an input/output module 220 for receiving and outputting audio signals, and a storage module 222 which may include memory for storing executable instructions thereon and which may also include a buffer for storing audio signals. The processing module 218, input/output module 220, and storage module 222 may be configured to implement the conversion of sound described in FIG. 1.

In another aspect, a signal from the microphones may be captured for use in medical monitoring. For example, a microphone located on one or more locations on the patient such as on the skin above the larynx, or a microphone located on a portion of the ventilator near the patient such as on the mouthpiece 210 of the noninvasive ventilator shown in FIG. 2, or on an oral intubation tube of an intubated patient, can detect not only vocal sound waves, but also sound waves associated with endogenous patient functions. Functions of interest may include swallowing, heartrate, coughing or other sounds associated with fluid in an airway, sounds associated with patient-induced inhalation, exhalation, a pause in breathing, or any other suitable sound produced by a patient. In some cases, a pulse oximeter can be included in one or more components of a microphone and/or ventilator, such as in a mask of a non-invasive ventilator system. The pulse oximeter may be functional to determine one or more of the blood oxygenation level and pulse rate, and may further be used to detect abnormalities in ventilator function. For example, a change in pulse rate or blood oxygenation detected by the pulse oximeter may cause the system to issue an alarm indicating the abnormality.

In some cases, a signal from a microphone for use adjacent to the vocal folds may be used in conjunction with monitoring the pulse and/or non-speech airway sounds for determining a sensor-placement position for the first sensor 204. For example, one suitable position for the placement of a microphone on the neck of a patient which is proximate to the vocal folds is also proximate to the carotid artery. By monitoring the volume of a sound corresponding to the pulse via the carotid artery, a practitioner can achieve repeatable and optimal placement of a microphone near the vocal folds. In some cases, a regular sound of airflow through the trachea can also be used as a guide to determine an optimal microphone position.

In some aspects, the audio signals obtained from the first and second sensors 204, 212 can be combined. For example, audio frequencies associated with high-pitched sibilance (such as the sounds associated with the letters 'c', T, and 's') may be less amenable to detection using a transducer attached with a throat of a patient near the vocal folds. By selectively acquiring said frequencies via a transducer located on or in a mask of a noninvasive ventilator device, the system 200 can recombine portions of the audio signals acquired from the first and second sensors 204, 212 in order to reproduce sounds that better match the original human voice. For example, the throat mounted transducer can capture frequencies in formant $f_1$. Formant $f_1$ is the lower register of human speech which ranges from about 300 Hz to 750 Hz. The upper formant, $f_2$, spans the frequency range from 900 Hz to about 3000 Hz. This higher range is the region of much greater intelligibility. The upper formant range represents about 57% of the intelligibility of the vocal audio spectrum. By employing additional transducers to capture vocalizations from the mask, and processing the signal to remove respirator artifacts, the intelligibility of the output can be increased significantly. Through the mask mounted microphone, sibilance and harmonics can also be captured. These vocal components generally occur in the 5000 Hz to 8000 Hz range, and provide the human portion of vocalizations that distinguishes human speech from machine speech. Respiratory apparatus audio spectrum can be wide-band, similar to pink noise. Squelching respiratory noise can be accomplished, for example, both by filtering the signal to eliminate frequencies below about 300 Hz and above 3000 Hz, and by employing a sensor, or input from the respiratory equipment, to detect an inhalation cycle, and synchronize a gain reduction event to coincide with the cycle. For example, a rate of airflow that can be produced by a patient with weakened lung function may be insufficient to produce audible speech through the vocal cords without amplification; therefore the signal associated with the first sensor 204 can be cleaned by use of one or more suitable audio filters and amplified to reproduce the low-range and mid-range of human speech. Concomitantly, the signal associated with the second sensor 212 can be cleaned by use of one or more filters such as a high-pass filter and amplified to reproduce sibilance associated with the same speech, and the two signals can be recombined. The balance of sibilance, low-range, and mid-range sounds in speech may be skewed in a patient with poor lunch function; therefore, the system can also recombine said aspects of speech according to different amplification factors in each case. For example, sounds associated with sibilance can be disproportionately loud compared to sounds associated with vocal fold vibration, and may be amplified at a lower gain than the sounds associated with vocal fold vibration.

In some aspects, audio signals can also be obtained from a third sensor associated with the ventilator device and configured to listen to the sounds associated with pressure originating from the device. In some cases, this third audio signal can be used to discriminate between sounds associated with the pressure originating from the device and the sibilance of patient speech. In some cases, a noise-cancellation algorithm can be applied to the sounds obtained from the second sensor 212 using sounds associated with the device so as to isolate sibilance of patient speech.

In some cases, obtaining and/or isolating sibilance of patient speech can also include de-essing, or attenuating the high amplitudes associated with recording certain sibilance. For example, sounds associated with 's' and 'c', in particular, can have very high relative amplitude in an audio recording. The system 200 can be configured to include multiple filter stages for selectively reducing multiple narrow frequency ranges associated with particular sibilance. In some cases, the system may include preset filter arrangements and gains associated with vocal frequency ranges of particular classes of persons based on age, male/female, adult/child; and the configuration may include a global sliding scale for overall pitch. For example, a typical vocal mid-range and low-range may vary significantly between adult and child voices, whereas a vocal high-range (as for sibilance) may vary less between adult and child voices; accordingly, a difference between the filters selected for obtaining the mid-range and low-range in these two cases may be greater than a difference between the filters selected for obtaining the high-range.

In some aspects, a signal from one or more microphones may be used to detect changes in function and/or abnormalities in the function of the ventilator device. For example, the first sensor 204 located near the vocal folds may be useful for detecting sounds associated with swallowing, choking, wheezing or other indicia of patient distress. The second microphone 212 may likewise be used to detect the sound of air escaping the mask 210 in order to detect, for example, a poor seal or a leak around the mask periphery, poor respiration, panicked or increased respiration, low airflow or blocked airflow, or other suitable parameter of function that can manifest in a change in flow rate into or out of the mask 210.

In another aspect, a signal from the microphones can be used to detect when the patient attempts to begin speaking or begins to produce any suitable vocalization. For example, a sound waveform associated with vocalization may appear different than sound waveforms associated with breathing, forced airflow, and endogenous patient sounds. A beginning of a vocalization can be determined by monitoring a vocal frequency or a range of frequencies associated with speech. In some other cases, a beginning of a vocalization can be determined by monitoring a pattern of one or more endogenous sounds and detecting, for example, when a patient attempts to pause between breaths. In some aspects, the vocal frequency may be dependent upon the patient and a technician or practitioner may perform a calibration step to identify and frequency range associated with speech for the particular patient. In some other aspects, a range or tonal quality associated with speech may be a predetermined range. In some cases, detecting the beginning of a vocalization may cause the system to provide an alert. For example, in some cases a sound or alarm may be issued from one or more of the speakers when a patient begins to speak. In some other cases, a non-auditory signal or alarm may also be provided, such as an electrical signal for causing an indicator light, a message, or an instruction to a medical device.

In some aspects, the system may provide a signal to a medical device in order to facilitate a change in the function of the ventilator, for example, to better facilitate patient speech. In some cases, as in with a CPAP device or other noninvasive ventilator device, sounds associated with the beginning of a vocalization can cause the ventilator to temporarily (e.g., momentarily or for a period of seconds) reduce the rate of airflow so as to reduce the noise associated with said airflow and/or to reduce the airway pressure that the patient must fight in order to vocalize. In some cases, sounds associated with the beginning of vocalization can also be used to alter the function of an invasive ventilator device.

Figure 3:
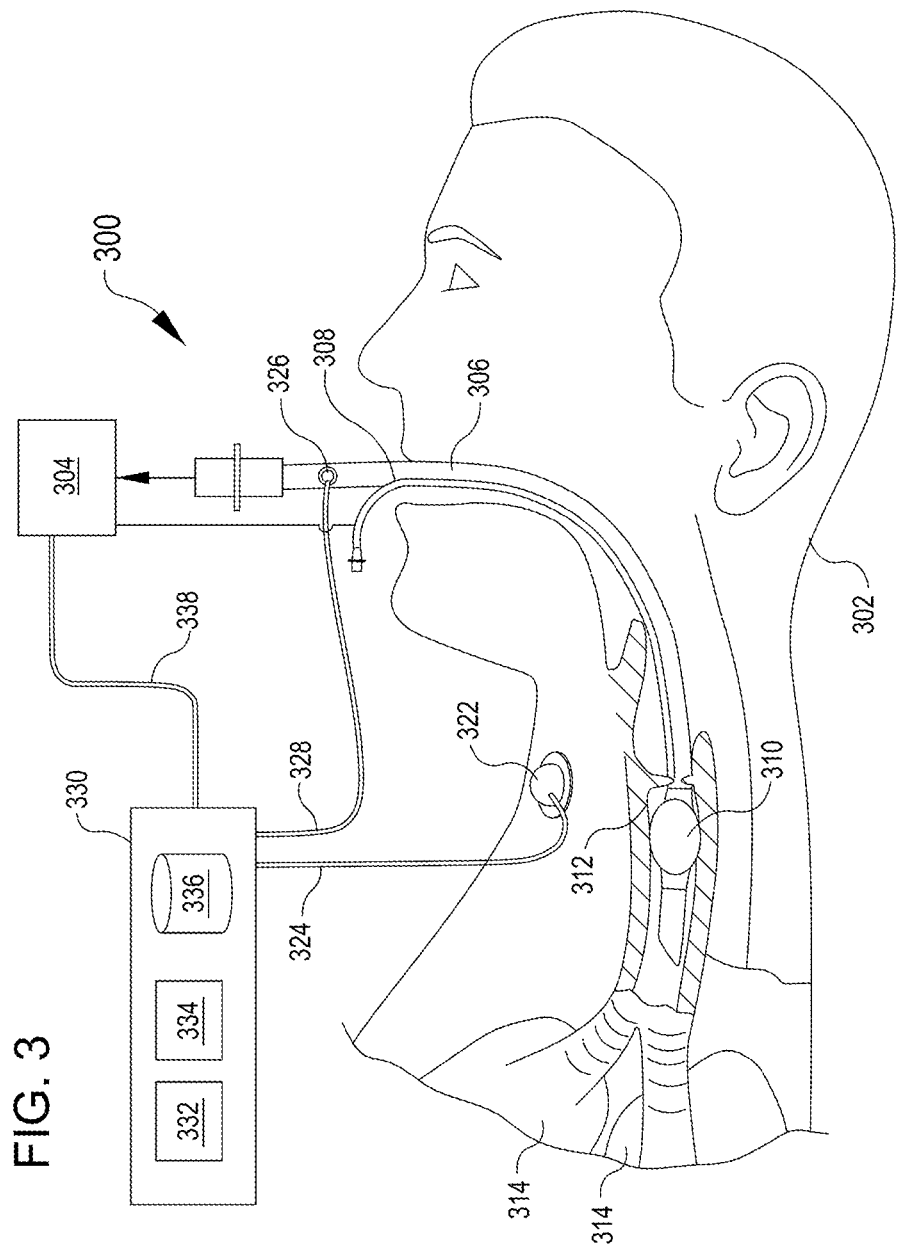
FIG. 3 is a perspective view of an exemplary speech enhancement system for use with a ventilator that includes intubating a patient, in accordance with embodiments.

FIG. 3 shows an exemplary speech enhancement system 300 for use with a ventilator 304 that includes tracheal intubation, in accordance with embodiments. In the speech enhancement system 300, a patient 302 can be intubated via the trachea 312 with an endotracheal tube 306 and cuff controller 308 which can be inserted into the entry of the patient's lung 314. The endotracheal tube 306 terminates at or near an inflatable cuff 310 which can be controlled via the cuff controller 308 which, in some embodiments, is a tube for inflating the cuff 310. The system 300 further includes a first sensor 322 connected with the patient near the vocal folds and connected (e.g., via a lead 324) with the processing unit 330, and with a second sensor 326 positioned near the patient's mouth and connected (e.g., via a lead 328) with the processing unit. The processing unit 330 can also be connected (e.g., via a lead 338) with the ventilator 304. The processing unit 330 can include at least a processing module 336 for processing audio signals as described in FIG. 1 and FIG. 2; an input/output module 334 for receiving audio signals from the various sensors and for outputting audio signals; and a storage module 336 for storing executable instructions, which can also act as a buffer for storing audio signals for processing and for output.

In some aspects, the system 300 may provide a signal to the ventilator 304 serving the patient 302 with an intubated airway, in order to partially deflate the inflatable cuff 310. Partially deflating the cuff 310 can permit the patient 302 to exhale through the airway past the cuff in order to pass air over the vocal folds in order to vocalize. These aspects may be combined with aspects that include multiple microphones, with additional microphones for example attached with the endotracheal tube near the mouth, for detecting non-vocal sound waves associated with the rushing air in order to enable the system to separate and cancel said non-vocal sounds, as described above in reference to FIG. 2. In some cases, the signal provided to the ventilator 304 can also cause the ventilator to reduce a flow rate or a pressure temporarily, so as to ease the pressure that a patient must fight in order to vocalize.

Figure 4:
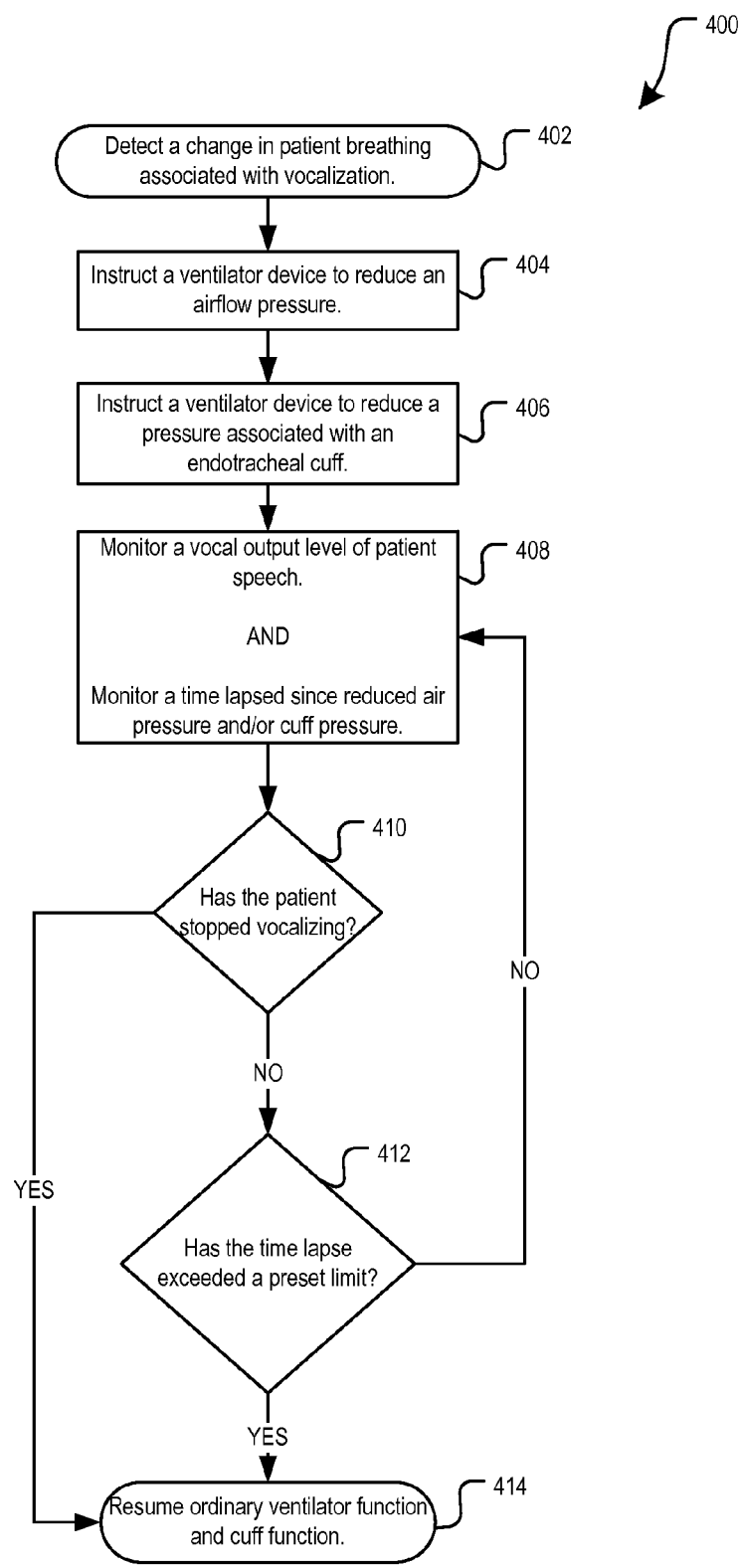
FIG. 4 is an example process flow diagram for implementing the system shown in FIG. 3.

For example, FIG. 4 shows a simplified process flow diagram for an example process 400 for controlling a speech enhancement system such as the system 300 of FIG. 3. In the process 400, the system detects a change in patient breathing associated with vocalization (402). In some cases, this change in patient breathing may be detected by detecting a sound caused by the patient attempting to inhale, pause, or clear their airway. This change may also include an alteration in the pattern of a regular airflow cycle caused by the patient attempting to inhale, exhale, or pause in-between breaths. The system can then cause a ventilator device to reduce an airflow pressure associated with the positive airflow ordinarily provided by the ventilator (404). In some cases, such as where the ventilator is a non-invasive ventilator such as a CPAP machine, the degree of reduction can include any suitable degree of partially shutting off the airflow or fully shutting off the airflow. Where the system includes endotracheal intubation, the system can cause a ventilator to reduce the pressure in an endotracheal cuff, so as to permit some air to escape from the lungs around the cuff and enable the intubated patient to vocalize (406). In some cases, the degree of deflation may be approximately 5%, 10%, 15%, 20%, or more; or in some cases, the degree of deflation may be controllable from the ventilator device or from the processing unit of a speech enhancement system such as the system 300 shown in FIG. 3. While the ventilator is operating at reduced pressure, and/or while the ventilator has reduced the pressure to an endotracheal cuff, the system can monitor a vocal output originating from the patient and can, in some cases, also monitor a time elapsed since the air pressure of the airflow and/or the air pressure of the cuff was reduced (408). If it is determined that the patient has stopped vocalizing or attempting to vocalize (410), the system can resume ordinary operation of the ventilator and/or the endotracheal cuff (414). If the patient continues to vocalize, the system can check whether the time that has elapsed has exceeded a preset limit (412). If the time elapsed has exceeded a limit, the system can resume ordinary ventilator and cuff function (414); and otherwise, the system can continue to monitor the vocal output of the patient and the time elapsed (408).

INDUSTRIAL APPLICABILITY

Among the features and attributes of the present invention are:

Exceptional sensitivity to allow even very weak patients to communicate;

Smooth surface(s) for the user interface and/or audio output transducer permit cleansing with liquid disinfectant;

Signal dynamics modulation to mitigate loud sounds such as coughing and transducer impact;

Elimination of sounds caused by air movement from respiratory devices;

Signal enhancement to provide intelligibility;

Signal conditioning to prevent audio feedback;

Various controls to adjust signal processing to optimize signal conditioning for individual patients;

Additional user tactile feedback via haptics;

System to have no interference or effect on respiratory equipment, masks, or pulmonary treatments;

Signal conditioning electrical architecture to allow changes in signal path through the various signal conditioning sections to provide flexibility in tuning and optimization to various patients;

Auxiliary interfaces to provide integration with existing patient monitoring systems;

Auxiliary telephone interface provides muting control to provide for private communication; and Auxiliary headphones to listen to patient.

The instant speech enhancement system will be of immediate use to persons who are using machines to help them breathe such as C-PAP, A-PAP, and Bi-PAP. The instant speech enhancement system will also be of utility and therefore of interest in other situations such as in a work environment where a respiratory mask must be worn for protection against airborne contaminants.

Because of its ability to run on battery power, the instant communication and speech enhancement system is not tethered to AC "house current", but instead is highly portable. Thus, the system can be provided to ambulance, fire, police and other emergency first responders, to automobiles, to bicycles, to wheelchairs and power chairs, and to public transit system such as aircraft, trains including subway systems, buses and motor vehicles for hire such as taxis.

An artisan of ordinary skill will appreciate that various modifications may be made to the invention herein described without departing from the scope or spirit of the invention as defined in the appended claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system to enhance verbal communication ability of a patient using a respiratory apparatus, the system comprising:
    a first transducer configured to be coupled with a patient adjacent to the patient's throat, the first transducer being configured to convert sounds into a first signal; and
    a processing unit operatively coupled with the first transducer to receive the first signal, the processing unit comprising at least a processor and memory containing executable instructions thereon, the executable instructions, when executed by the at least one process or, cause the at least one processor to:
        filter the first signal to remove frequencies within an audible range that are not associated with human speech to create a first processed signal;
        generate an output signal based on the first processed signal; and
        output the output signal to an audio output device configured to covert the output signal into audio output.

2. The system of claim 1 wherein the first transducer is a high-gain optical transducer.

3. The system of claim 1 further comprising a second transducer operatively coupled with the processing unit and configured to be supported adjacent to the patient, the second transducer being configured to convert sounds into a second signal; and
    wherein the executable instructions are further configured to cause the at least one processor to:
        filter the second signal to remove frequencies not associated with human speech to create a second processed signal;
        combine the first and second processed signals to generate a combined processed signal;
        generate the output signal based on the combined processed signal.

4. The system of claim 1 further comprising a second transducer operatively coupled with the processing unit and configured to be supported adjacent to the patient, the second transducer being configured to convert sounds into a second signal; and
    wherein the executable instructions are further configured to cause the at least one processor to:
        modify the first processed signal based in part on the second signal.

5. The system of claim 4, wherein the second transducer is further configured to detect sounds associated with the operation of the respiratory apparatus; and
    wherein the executable instructions are further configured to cause the at least one processor to:
        filter the second signal to remove frequencies not associated with the operation of the respiratory apparatus to create a second processed signal; and
        modify the first processed signal by cancelling a portion of the first processed signal based in part on the second processed signal.

6. The system of claim 4, wherein the second transducer is arranged in proximity to the mouth of the patient; and
    wherein the executable instructions are further configured to cause the at least one processor to:
        filter the second signal to remove frequencies not associated with sibilance of human speech to create a second processed signal; and
        modify the first processed signal in part by adding a portion of the second processed signal to the first processed signal.

7. The system of claim 6, wherein the executable instructions are further configured to cause the at least one processor to:
    perform a de-essing operation on the second processed signal.

8. The system of claim 4, wherein the second transducer is arranged in proximity to the respiratory apparatus; and
    wherein the executable instructions are further configured to cause the at least one processor to:
        detect a frequency associated with an abnormal operation of the respiratory apparatus; and
        provide an alert for presentation to a user indicating that abnormal operation of the respiratory apparatus has occurred.

9. The system of claim 1, wherein the executable instructions are further configured to cause the at least one processor to:
    detect, via the first signal, an audio signal waveform associated with respiratory distress; and
    provide an alert for presentation to a user indicating that respiratory distress has been detected.

10. The system of claim 1, further comprising a pulse oximeter; and
    wherein the executable instructions are further configured to cause the at least one processor to:
        receive information concerning one or more of a heart rate and a blood oxygen saturation of a patient via the pulse oximeter;
        detect that one or more of the heart rate and blood oxygen saturation has fallen below a predetermined limit based in part on the information; and
        provide an alert for presentation to a user based in part on the detecting.

11. The system of claim 1, further comprising the respiratory apparatus, wherein
    the respiratory apparatus is configured to provide a flow of air to the patient; and
    the executable instructions are further configured to cause the at least one processor to cause the respiratory apparatus to adjust a flow rate of the flow of air to the patient based in part on the first signal.

12. The system of claim 11, wherein adjusting the flow rate further comprises reducing the flow rate such that the flow of air can be overcome by a person with diminished lung function in order to vocalize.

13. The system of claim 11, wherein the executable constructions are further configured to cause the at least one processor to:
    detect a vocalization based in part on the first signal; and
    cause the respiratory apparatus to reduce the flow rate in response to detecting the vocalization.

14. The system of claim 13, wherein the executable constructions are further configured to cause the at least one processor to:
    determine a duration of the vocalization based in part on the first signal;

detect that the duration of the vocalization has exceeded a predetermined maximum duration; and cause the respiratory apparatus to increase the flow rate in response to detecting that the duration has exceeded the maximum duration.

15. The system of claim 11, wherein the respiratory apparatus further comprises an endotracheal cuff; and wherein the executable constructions are further configured to cause the at least one processor to cause the endotracheal cuff to decrease in volume.

16. A method, comprising:

receiving a first audio signal from a first transducer attached with a patient near the neck of the patient;

receiving a second audio signal from a second transducer supported near the patient and proximate to one or more elements of a respiratory apparatus that provides the patient with a flow of air;

filtering the first audio signal by removing one or more ranges of audible frequencies not associated with human vocalization to create a first filtered signal;

filtering the second audio signal by removing one or more ranges of frequencies not associated with sibilance in human speech to create a second filtered signal;

amplifying the first filtered signal to create a first processed signal;

modifying the first processed signal based in part on the second filtered signal;

generating an output signal based on the first processed signal; and outputting the output signal to an audio output device configured to covert the output signal into audio output.

17. The method of claim 16, further comprising:

filtering the second audio signal by removing one or more ranges of frequencies not associated with operation of the respiratory apparatus to create the second filtered signal; and generating the output signal by cancelling a portion of frequencies in the first processed signal based on the second filtered signal.

18. The method of claim 16, further comprising:

detecting a pause in a pattern of breathing based in part on the first signal; and causing the respiratory apparatus to reduce a rate of the flow of air in response to detecting the pause.

19. The method of claim 16, further comprising:

balancing the first and second filtered signals.

20. The method of claim 19, further comprising;

receiving a third audio signal from a third transducer connected with the respiratory apparatus; and generating the output signal by cancelling a portion of frequencies in the first and second filtered signals associated with the third audio signal.

* * * * *